United States Patent
Itsuji et al.

(10) Patent No.: US 10,879,281 B2
(45) Date of Patent: Dec. 29, 2020

(54) IMAGE CAPTURE DEVICE, METHOD OF CAPTURING IMAGE WITH THE SAME, AND IRRADIATION DEVICE

(71) Applicant: CANON KABUSHIKI KAISHA, Tokyo (JP)

(72) Inventors: Takeaki Itsuji, Hiratsuka (JP); Noriyuki Kaifu, Atsugi (JP)

(73) Assignee: Canon Kabushiki Kaisha, Tokyo (JP)

(*) Notice: Subject to any disclaimer, the term of this patent is extended or adjusted under 35 U.S.C. 154(b) by 61 days.

(21) Appl. No.: 16/403,279

(22) Filed: May 3, 2019

(65) Prior Publication Data
US 2019/0259791 A1 Aug. 22, 2019

Related U.S. Application Data

(63) Continuation of application No. PCT/JP2017/041330, filed on Nov. 16, 2017.

(30) Foreign Application Priority Data

Nov. 28, 2016 (JP) .................. 2016-230606

(51) Int. Cl.
*H01L 27/146* (2006.01)
*H04N 5/225* (2006.01)
(Continued)

(52) U.S. Cl.
CPC .......... *H01L 27/14605* (2013.01); *A61B 5/05* (2013.01); *G01N 21/01* (2013.01);
(Continued)

(58) Field of Classification Search
None
See application file for complete search history.

(56) References Cited

U.S. PATENT DOCUMENTS

| 2005/0023470 A1 | 2/2005 | Ferguson |
| 2007/0228280 A1 | 10/2007 | Mueller |

(Continued)

FOREIGN PATENT DOCUMENTS

| JP | 2006-81771 A | 3/2006 |
| JP | 2011-203253 A | 10/2011 |

(Continued)

*Primary Examiner* — Alexander G Ghyka
(74) *Attorney, Agent, or Firm* — Canon U.S.A., Inc. IP Division

(57) ABSTRACT

An image capture device 1001 captures an image by using a terahertz wave and includes a generating unit 112 that includes a plurality of generation elements each of which generates the terahertz wave and rests on a resting plane 117, an irradiation optical system 111 that irradiates an object with the terahertz wave, an imaging optical system 101 that images the terahertz wave that is reflected from the object, and a sensor 102 that includes pixels. The plurality of generation elements include at least a first generation element 113 and a second generation element 114 that have different angles of radiation to the object. There is an overlap region in which a region of radiation of a first terahertz wave 156 from the first generation element to the object overlaps a region of radiation of a second terahertz wave 157 from the second generation element to the object.

17 Claims, 16 Drawing Sheets

(51) Int. Cl.
*H04N 5/341* (2011.01)
*G01N 21/3581* (2014.01)
*A61B 5/05* (2006.01)
*G01S 13/89* (2006.01)
*G01N 21/01* (2006.01)

(52) U.S. Cl.
CPC .......... *G01N 21/3581* (2013.01); *G01S 13/89* (2013.01); *H04N 5/2254* (2013.01); *H04N 5/341* (2013.01)

(56) References Cited

U.S. PATENT DOCUMENTS

| | | | |
|---|---|---|---|
| 2009/0290149 A1 | 11/2009 | Roth | |
| 2012/0032081 A1* | 2/2012 | Itsuji | G01J 3/108 250/340 |
| 2015/0214415 A1* | 7/2015 | Takenaka | G01N 21/3581 250/330 |
| 2018/0031469 A1* | 2/2018 | Aiko | H01S 3/0092 |
| 2018/0224489 A1* | 8/2018 | Velthaus | G01R 27/28 |
| 2018/0335682 A1* | 11/2018 | Satoh | G01N 21/3586 |
| 2019/0041326 A1* | 2/2019 | Watanabe | G01J 3/42 |
| 2019/0154575 A1* | 5/2019 | Peng | G01J 5/08 |
| 2019/0190223 A1* | 6/2019 | Jeong | H01J 63/02 |
| 2019/0331594 A1* | 10/2019 | Klose | G01N 21/952 |
| 2020/0182783 A1* | 6/2020 | Jun | G01N 21/3586 |

FOREIGN PATENT DOCUMENTS

| | | |
|---|---|---|
| JP | 2012-26943 A | 2/2012 |
| JP | 2012-37293 A | 2/2012 |
| JP | 2013-215342 A | 10/2013 |
| JP | 2014-161484 A | 9/2014 |
| JP | 2015-141111 A | 8/2015 |
| WO | 02/017231 A2 | 2/2002 |
| WO | 2005/112130 A2 | 11/2005 |
| WO | 2013-148368 A1 | 10/2013 |
| WO | 20016/031181 A1 | 3/2016 |

* cited by examiner

US 10,879,281 B2

IMAGE CAPTURE DEVICE, METHOD OF CAPTURING IMAGE WITH THE SAME, AND IRRADIATION DEVICE

CROSS-REFERENCE TO RELATED APPLICATIONS

This application is a Continuation of International Patent Application No. PCT/JP2017/041330, filed Nov. 16, 2017, which claims the benefit of Japanese Patent Application No. 2016-230606, filed Nov. 28, 2016, both of which are hereby incorporated by reference herein in their entirety.

TECHNICAL FIELD

The present invention relates to an image capture device that uses terahertz waves, a method of capturing an image with the image capture device, and an irradiation device.

BACKGROUND ART

Terahertz waves are electromagnetic waves that typically have components in a frequency band from 0.3 THz to 30 THz. In the frequency band, there are many kinds of characteristic absorption that originate from the structure and state of various substances, starting with biomolecules and resins. In addition to this, the wavelength thereof is longer than those of visible light and infrared light. Accordingly, terahertz waves are unlikely to be affected by scattering and have high permeability against many substances. The wavelength is shorter than those of millimeter waves, and spatial resolution is high.

There are expectations of applications to, for example, a safe imaging technique in place of X-rays and a high resolution transmission imaging technique in place of millimeter waves (typically, 30 GHz to 300 GHz) and a spectrum imaging technique achieved by making the best use of the above characteristics. For example, applications to a concealed-object inspection technique such as a security check or a surveillance camera in public is considered.

PTL 1 discloses that an image capture device uses a terahertz wave irradiation device, beams of terahertz waves from a terahertz wave generation element that is considered as a point light source are enlarged and radiated to an object, and the terahertz waves are received by detector arrays.

CITATION LIST

Patent Literature

PTL 1: Japanese Patent Laid-Open No. 2006-81771

SUMMARY OF INVENTION

An image capture device according to an aspect of the present invention captures an image of an object by using a terahertz wave and includes a generating unit that includes a plurality of generation elements each of which generates the terahertz wave and rests on a resting plane, an irradiation optical system that images the terahertz wave from the generating unit on an imaging plane, an imaging optical system that images the terahertz wave that is reflected from the object, and a sensor that includes pixels and that detects the terahertz wave from the imaging optical system. The generating unit rests on an object plane of the irradiation optical system. The plurality of generation elements include at least a first generation element and a second generation element that are adjacent to each other in the generating unit and that have different angles of radiation to the object. There is an overlap region in which a beam of a first terahertz wave from the first generation element to the object and a beam of a second terahertz wave from the second generation element to the object overlap on the imaging plane.

Further features of the present invention will become apparent from the following description of exemplary embodiments with reference to the attached drawings.

DESCRIPTION OF EMBODIMENTS

The skin structure of the human body has irregularities of several 10 μm to several 100 μm. The wavelength of terahertz waves is in the range from several 10 μm to several 100 μm or more than the range as with the skin structure. For this reason, in the case where an object includes the human body, imaging with the terahertz waves is not scattering imaging with scattering of, representatively, visible light but is specular reflection imaging with specular reflection. More specifically, the skin structure of the human body can be considered as a smooth reflective object against the terahertz waves. The direction of the specular reflection waves of the terahertz waves is determined by the position and angle at which the terahertz waves are incident on a curved surface of the human body.

For example, in an attempt to image the human body with an image capture device that radiates the terahertz waves by using a point light source disclosed in PTL 1, the specular reflection waves of the terahertz wave do not reach the detector arrays depending on the direction of the specular reflection waves of the terahertz waves. For this reason, some of pixels of the image capture device can detect the terahertz waves, but the other pixels cannot detect the terahertz waves in some cases. As the ratio of the pixels that cannot detect the terahertz waves increases, information about the shape of the object decreases, and it is not easy to presume the detailed shape of the object from a captured image.

In view of the above problem, it is an object of embodiments described later to inhibit the number of pixels that can detect terahertz waves from decreasing in an image capture device that uses the terahertz waves.

According to each embodiment described later, the image capture device that uses the terahertz waves can inhibit the number of the pixels that can detect the terahertz waves from decreasing.

According to each embodiment described later, an irradiation device that radiates the terahertz waves and the image capture device that uses the irradiation device will be described. The terahertz waves will now be described.

Figure 13:
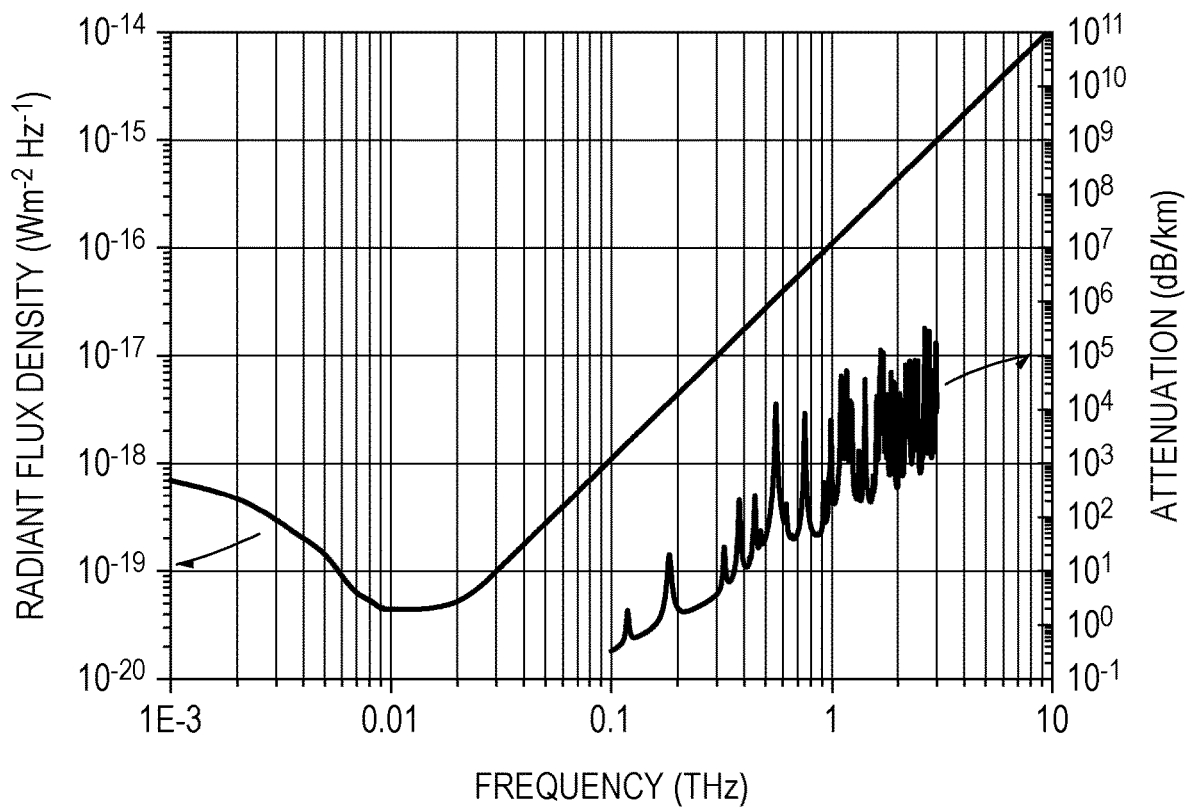
FIG. 13 illustrates background noise and atmospheric attenuation of electromagnetic waves.

FIG. 13 illustrates an example of background noise (radiant flux density) that originates from the sun and comes to the earth in a microwave band to a terahertz wave band, and an example of a frequency spectrum of the amount of atmospheric attenuation in the terahertz wave band. A noise at an increased part of the background noise that is observed in the microwave band to a millimeter wave band varies depending on the state of the activity of the sun. As illustrated in FIG. 13, in some cases, the background noise increases in the microwave band to the millimeter wave band. In the microwave band to the millimeter wave band, an artificial noise due to the activity of a human being and various noises due to the state of the weather and the atmosphere are superposed as environment noises.

In recent years, communication technology mainly in the millimeter wave band and astronomical observation with electromagnetic waves in the millimeter wave band have become popular, and the radio law divides a frequency band of less than 0.275 GHz into fine sections for purposes. The electric field strength that can be outputted in the millimeter wave band is strictly restricted by the radio law because this band is also used for the astronomical observation.

In the case where an image capture device that uses the millimeter waves is constructed, a frequency conversion technique that uses a multiplier and a signal that has a small SN ratio is frequently used for detection because of increase in the background noise and restriction of the outputs of the millimeter waves that can be used. In addition, the wavelength of the electromagnetic waves that are used is long, the size of an optical system that includes an image sensor increases, and there is a concern that the size of the image capture device increases electrically and optically. For some use, a sufficient SN ratio cannot ensured, and it is necessary for a pixel size of the image sensor to be increased. Accordingly, an image that is captured is limited to the entire contour of the object, and it is difficult to directly identify the detailed shape of the object in some cases.

The use of the image capture device that uses the terahertz waves can be considered to make an image of a millimeter wave camera more precise. For example, it can be expected that the image capture device that uses the terahertz waves can use a light source that has a higher output than that in the case where the millimeter waves are used, there are many choices of usable frequencies, and the device size can be decreased because the wavelength is decreased.

As seen from the spectrum of the amount of atmospheric attenuation in the terahertz wave band in FIG. 13, there is a region (referred to as an "atmospheric window") in which the atmospheric attenuation is small. Accordingly, it can be considered that selecting the electromagnetic wave related to the atmospheric window enables great signal attenuation to be prevented from occurring.

According to the embodiments described later, the image capture device that uses the terahertz waves, a method of capturing an image, and the irradiation device that is used in the image capture device will be described. The object of each embodiment described later is to inhibit the number of the pixels that can detect the terahertz waves from decreasing even in the image capture device that uses the terahertz waves for specular reflection imaging as described above. An image capture device that uses the millimeter waves potentially has the same problem. However, the problem more notably surfaces when the shape of the object is imaged with high precision by using the image capture device that uses the terahertz waves and that achieves higher resolution than the image capture device that uses the millimeter waves and that images the entire contour of the object.

First Embodiment

Figure 1A:
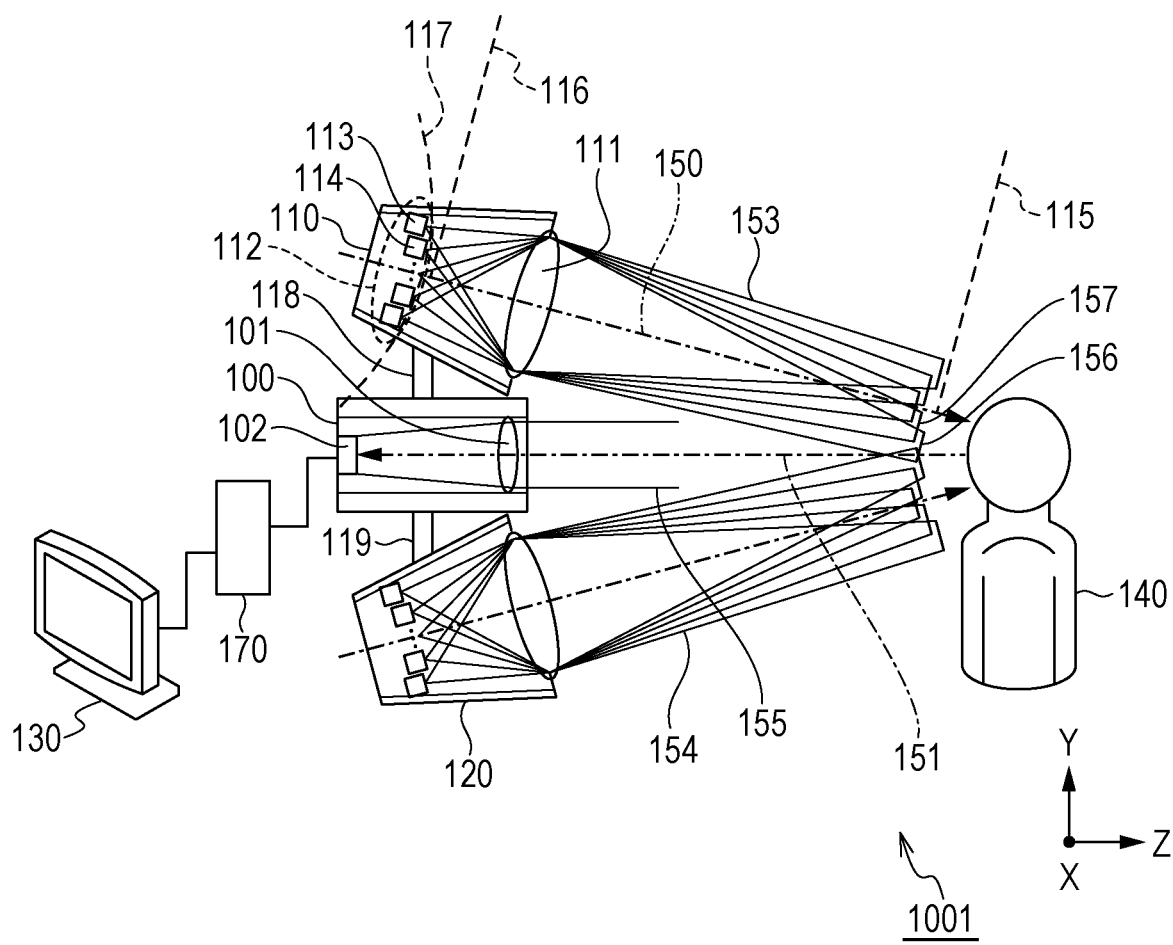
FIG. 1A schematically illustrates the structure of an image capture device according to a first embodiment.

An image capture device 1001 according to the present embodiment will be described with reference to FIG. 1. FIG. 1 schematically illustrate the structure of the image capture device 1001.

The image capture device 1001 includes a detection unit 100, a first irradiation device (first irradiation unit) 110, a second irradiation device (second irradiation unit) 120, a first support unit 118, a second support unit 119, a monitor unit 130, and a processing unit 170.

The first irradiation unit 110 and the second irradiation unit 120 irradiate an object 140 with the terahertz waves. According to the present embodiment, the image capture device 1001 includes two irradiation units (irradiation devices) of the first irradiation unit 110 and the second irradiation unit 120. However, the number of the irradiation units is not limited thereto and may be 1 or 2 or more. The terahertz waves that are generated from the first irradiation unit 110 are radiated to the object 140 as first irradiation waves 153. The terahertz waves that are generated from the second irradiation unit 120 are radiated to the object 140 as second irradiation waves 154.

The frequency of the terahertz waves from the first irradiation waves 153 and the second irradiation waves 154 preferably includes a component in a frequency band or a single frequency in the range from no less than 0.3 THz and no more than 30 THz in which the frequency is not assigned. In the case where the object 140 includes the human body, many clothes have high permeability up to 1 THz. Accordingly, in the case of, for example, a concealed-object inspection, a frequency range of no less than 0.3 THz and no more than 1 THz is more preferable.

The first irradiation unit 110 and the second irradiation unit 120 each include at least a generating unit 112 that generates the terahertz waves and an irradiation optical system 111. The first irradiation unit 110 will be described later. The second irradiation unit 120 has the same structure.

The generating unit 112 includes generation elements that include a first generation element 113 and a second generation element 114 that generate the terahertz waves, and corresponds to a surface light source that rests on a resting plane 117.

The size of each generation element is less than the distance to the detection unit 100, and the generation element can be considered as a point terahertz wave source and is referred to below as a point light source. In other words, the generation element is a terahertz wave source the size of which is substantially the same as a size that can be resolved as an image by the detection unit 100 or is smaller than the size. In this case, it can be considered that the point light source generates a terahertz wave radially from a single point. The resting plane 117 will be described later. In the following description, each of the generation elements that include the first generation element 113 and the second generation element 114 is referred to as the "point light source", and the generating unit that includes the generation elements is referred to as the "surface light source".

Examples of each point light source can include a terahertz wave generation element of a semiconductor element such as a resonant-tunneling diode, and a photoexcitation terahertz wave generation element that uses optical switching and difference frequency light.

Each point light source preferably has an antenna structure to improve impedance matching with the air and the efficiency of generation of the terahertz waves. The size of an antenna is determined to be substantially equal to the wavelength that is used.

The first point light source 113 and the second point light source 114 that are included in the point light sources will be described below by way of example. The first point light source 113 generates a first terahertz wave 156. The second point light source 114 generates a second terahertz wave 157. There is an overlap region in which a region of radiation of the first terahertz wave 156 partly overlaps a region of radiation of the second terahertz wave 157.

In this case, the distance between the first point light source 113 and the second point light source 114 is preferably equal to or longer than a distance that is obtained from the longest wavelength of the wavelengths of the first terahertz wave 156 and the second terahertz wave 157. Specifically, the distance between the first point light source 113 and the second point light source 114 is equal to or more than a far field of each antenna that corresponds to the longest wavelength of the wavelengths of the first terahertz wave 156 and the second terahertz wave 157. The wavelength of the first terahertz wave 156 and the wavelength of the second terahertz wave 157 may be the same or may differ from each other.

The "far field" in the specification means a distance at which the point light sources 113 and 114 are considered to be separated from each other. The far field is expressed in various manners. For example, the far field is a distance of $2D^2/\lambda$ or more where D is the diameter of each antenna, and $\lambda$ is the wavelength of the terahertz waves. The distance between the point light sources is more preferably about $32D^2/\lambda$, which is considered as infinity. In a state where the second point light source 114 is disposed at the far field of the first point light source 113, the point light sources can be considered as independent light sources, and mutual effects between the point light sources can be ignored, which results in stable operation.

For example, in the case where half-wavelength antennas ($D=\lambda/2$) such as dipole antennas or patch antennas are used as the antennas of the point light sources 113 and 114, the far field can be calculated to be $0.5\lambda$ or more. In particular, the distance that is considered as infinity can be calculated to be $8\lambda$ or more. In the case where the first terahertz wave 156 and the second terahertz wave 157 are terahertz waves at 0.5 THz ($\lambda=0.6$ mm), the far field is 0.3 mm, the distance that is considered as infinity is 4.8 mm. In the case where the terahertz waves that are used have plural wavelengths, $\lambda$ is the longest wavelength.

The irradiation optical system 111 irradiates the object with the terahertz waves. The irradiation optical system 111 according to the present embodiment has an imaging function. Specifically, the first irradiation waves 153 that are generated from the surface light source 112 that rests on an object plane 116 of the irradiation optical system 111 are converged on an imaging plane 115 of the irradiation optical system 111. The object plane 116 is the imaging plane of the irradiation optical system 111 facing the object. The first irradiation waves 153 are combination waves of the terahertz waves that include at least the first terahertz wave 156 and the second terahertz wave 157. The number of the terahertz waves that are included in the combination waves is equal to the number of the point light sources that are included in the surface light source 112.

The irradiation optical system 111 may include a transmissive optical element such as a lens or a reflective optical element such as a mirror, or a combination thereof. For example, in the image capture device 1001 in FIG. 1, the irradiation optical system 111 the optical axis of which coincides with a straight line 150 includes a single lens. In the case where the lens is used as the irradiation optical system 111, the material of the lens preferably has a small loss against the terahertz waves that are used. Examples thereof include Teflon (registered trademark) and high density polyethylene. A method for visible light can be used for the design of the irradiation optical system 111.

Figure 2:
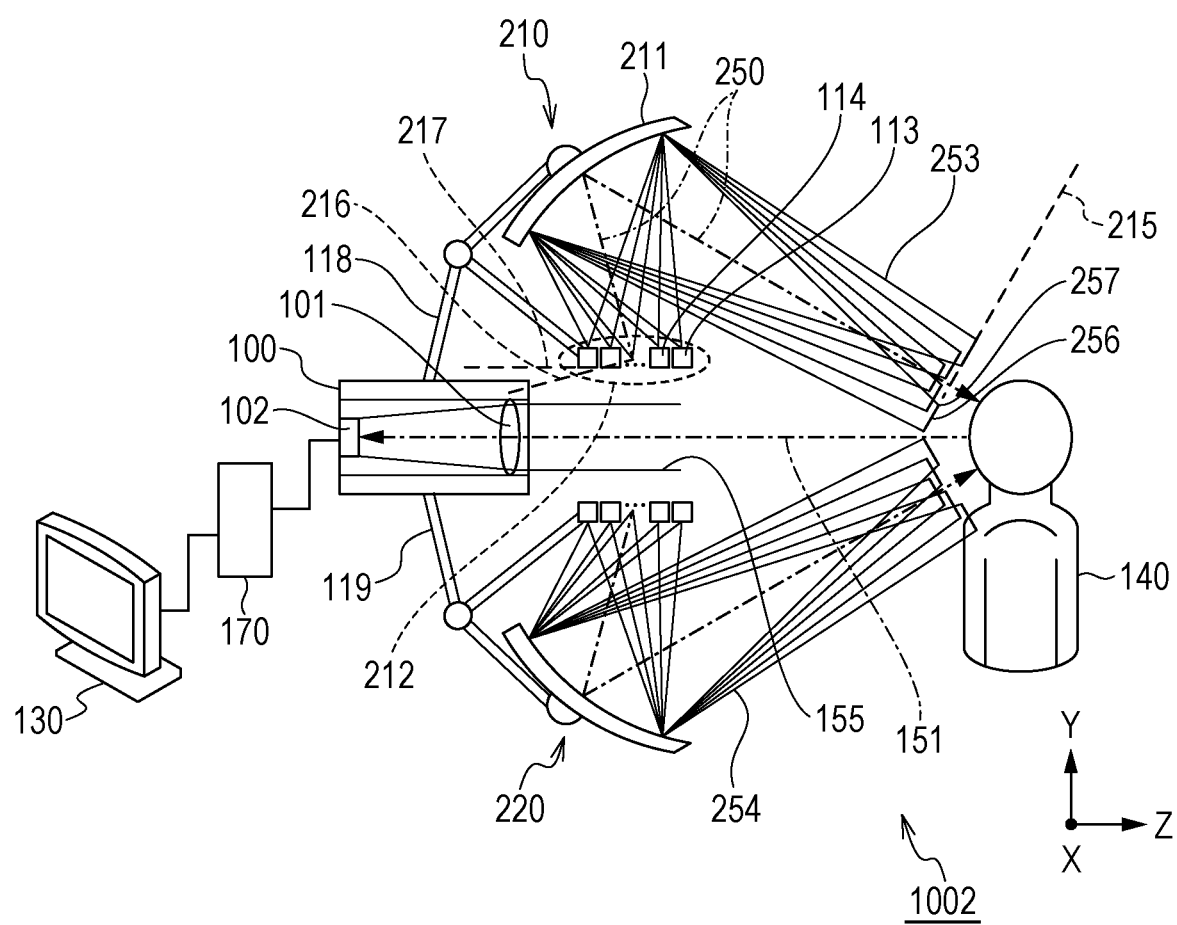
FIG. 2 schematically illustrates an example of another structure of the image capture device according to the first embodiment.

The structure of the irradiation optical system 111 is not limited to that of a transmissive optical system. For example, as illustrated in FIG. 2, a reflective irradiation optical system 211 that uses a mirror may be used as the irradiation optical system 111. The irradiation optical system 211 of an image capture device 1002 in FIG. 2 uses the mirror that reflects the terahertz waves from the point light sources, and the mirror has an off-axis paraboloid shape the optical axes of which coincide with straight lines 250. However, the structure of the mirror is not limited thereto.

In the image capture device 1002, a surface light source 212 includes the point light sources that rest on a resting plane 217 that intersects with an object plane 216 to adjust to the structure of the irradiation optical system 211. First irradiation waves 253 that include a first terahertz wave 256 from the first point light source 113 and a second terahertz wave 257 from the second point light source 114 via the irradiation optical system 211 are imaged on an imaging plane 215 and radiated to the object 140. A second irradiation unit 220 has the same structure. Second irradiation waves 254 from the second irradiation unit 220 are radiated to the object 140.

The use of the transmissive optical element illustrated in FIG. 1 as the irradiation optical system 111 enables the surface light source 112 and the irradiation optical system 111 to be coaxially arranged. For this reason, when the irradiation units 110 and 120 are constructed, the accuracy of alignment can be readily ensured. The coaxial arrangement enables an installation space to be decreased and enables the size of the irradiation units 110 and 120 to be decreased.

The use of the reflective optical element illustrated in FIG. 2 as the irradiation optical system 111 enables a loss when the terahertz waves pass through the optical element to be reduced and inhibits the outputs of the first irradiation waves 153 and the second irradiation waves 154 from decreasing. The size of a reflective optical system is easy to increase more than in the case of a transmissive optical system. Accordingly, the terahertz-wave-receiving area of the irradiation optical system 111 can be increased, and the efficiency of reception of the terahertz waves can be improved.

The detection unit 100 is a terahertz wave camera that detects the terahertz waves. In the image capture device 1001, the first irradiation unit 110 and the second irradiation unit 120 are secured to the detection unit 100 by using the first support unit 118 and the second support unit 119 and integrally formed. Each of the first support unit 118 and the second support unit 119 may include a posture adjustment movable portion that adjusts the postures of the first irradiation unit 110 and the second irradiation unit 120.

The detection unit 100 includes a sensor 102 that includes divided pixels and an imaging optical system 101 that images reflected waves 155, which are terahertz waves, from the object 140 on an imaging plane of the sensor 102. The reflected waves 155 include the second terahertz wave 157 and the first terahertz wave 156 that are reflected from the object 140.

The pixels of the sensor 102 are divided into an array shape or a matrix shape. The pixels include respective detection elements that detect the terahertz waves. Examples of each detection element can include a thermal detection element such as a bolometer or a semiconductor detection element such as a Schottky barrier diode. A terahertz wave image is formed with reference to an output signal of the sensor 102.

Each detection element of the sensor 102 preferably has an antenna structure to improve impedance matching with the air and the efficiency of detection of the terahertz waves. The size of each antenna is determined to be substantially equal to the wavelength that is used in the image capture device 1001. In the case where it is necessary to capture the image quickly, the semiconductor detection element is preferably used as the detection element.

The imaging optical system 101 images, on the sensor 102, an image of the object 140 that is on the object plane of the imaging optical system 101, and an optical element such as a lens or a mirror can be used. Each image capture device 1 uses a single lens the optical axis of which coincides with a straight line 151 as the imaging optical system 101. However, the structure of the imaging optical system 101 is not limited thereto, and plural optical elements may be used. In the case of the lens, a material that has a small loss against the terahertz waves that are used is preferably used. For example, Teflon and high-density polyethylene can be used. A method for visible light can be used for the design of the imaging optical system 101.

The reflected waves 155 from the object 140 are detected by the detection unit 100. The detection result of the detection unit 100 is sent to the processing unit 170. The processing unit 170 captures an image by using the detection result of the detection unit 100. Examples of the processing unit 170 can include a processing apparatus such as a computer that includes, for example, a CPU (central processing unit), a memory, and a storage device. A process for visualization may be performed by software in the processing unit 170. Some functions that are achieved by processes of the processing unit 170 can be substituted by hardware such as a logic circuit. The processing unit 170 may be a general-purpose computer or exclusive hardware such as a board computer or an ASIC. Alternatively, the processing unit 170 may be installed in the detection unit 100.

The monitor unit 130 can display the image of the object on the basis of information about the image that is formed by the processing unit 170. The monitor unit 130 may be a monitor of a computer that serves as the processing unit 170 or may be prepared to display the image.

Figure 1B:
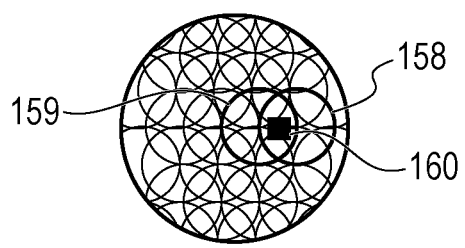
FIG. 1B schematically illustrates the structure of the image capture device according to the first embodiment.

FIG. 1B schematically illustrates a part of the imaging plane 115 of the irradiation optical system 111. The imaging plane 115 has an overlap region in which a part of a first beam distribution (first radiation region) 158 of the first terahertz wave 156 that is converged on the imaging plane 115 overlaps a part of a second beam distribution (first radiation region) 159 of the second terahertz wave 157 that is converged on the imaging plane 115. In the surface light source 112, the distance between the first point light source 113 and the second point light source 114 and the arrangement thereof are preferably adjusted such that the part of the first beam distribution 158 overlaps the part of the second beam distribution 159.

With this structure, a region of the object 140 is irradiated with the first terahertz wave 156 and the second terahertz wave 157 in different directions. Consequently, the first terahertz wave 156 and the second terahertz wave 157 are reflected from the object 140 at reflection angles that are equal to incident angles and travel in different directions from the object 140. This enables the first terahertz wave 156 and the second terahertz wave 157 that are reflected from the region of the object 140 to be considered as pseudo scattering waves.

At this time, the overlap region on the imaging plane 115 between the first beam distribution 158 and the second beam distribution 159 preferably overlaps an observation region 160 that corresponds to at least one of the pixels of the sensor 102 on the imaging plane 115.

In this way, each pixel of the sensor 102 of the detection unit 100 can receive specular reflection light in different directions from the corresponding observation region 160, and the percentage of the pixels that cannot detect the terahertz waves can be decreased. Consequently, the image can be captured by using the detection result of the detection unit 100 more accurately than in a conventional case. In addition, the shape of the object 140 can be presumed from the captured image more easily than in the conventional case.

The point light sources rest on the resting plane 117. The resting plane 117 may be a flat surface or may contain a curved surface. The resting plane 117 may be flush with the object plane 116 of the irradiation optical system 111 or may intersect therewith. The first irradiation unit 110 adjusts the shape of the resting plane 117 and the posture of the resting plane 117 with respect to the object plane 116 to adjust the distance between each point light source and the irradiation optical system 111, and adjusts aberration of the terahertz waves that are radiated to the object 140. The adjustment of the aberration of the terahertz waves enables the overlap region between the beam distributions of the terahertz waves from the point light sources to be adjusted and enables the degree of overlap with the observation region 160 to be adjusted.

Since the size of the irradiation optical system 111 is definite, there is a possibility that so-called vignetting occurs, that is, some of the terahertz waves are eliminated by the optical element of the irradiation optical system 111 depending on the shape of the resting plane 117 and the posture of the resting plane 117 with respect to the object plane 116. For example, the vignetting can decrease the outputs of the terahertz waves that reach the object 140. In order to reduce the vignetting, as illustrated in FIG. 3, a single point on the optical axis of an irradiation optical system 311 preferably intersects with a single point on a directional axis of a beam pattern (radiation pattern) of the terahertz wave that is radiated from each of the point light sources that include point light sources 313 and 314.

The directional axis of each point light source in the specification means the central axis of directional characteristics of the terahertz wave from the point light sources. Specifically, the directional axis coincides with a straight line that represents the direction in which the terahertz wave that has the maximum strength is emitted from the point light source. For example, the directional axis coincides with a straight line that connects positions at which the strength of the terahertz wave is maximum on concentric circles that have different radii and that have the center located at the center of gravity of the point light source.

Figure 3:
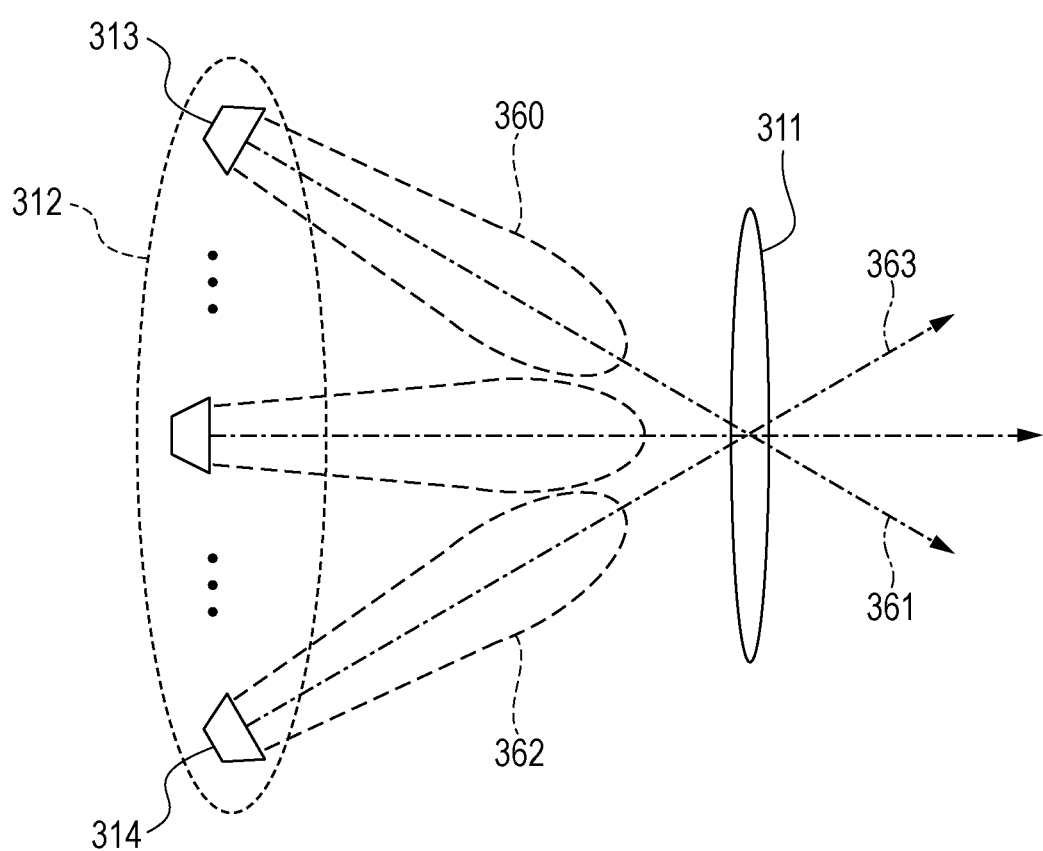
FIG. 3 schematically illustrates an example of arrangement of point light sources.

For example, as illustrated in FIG. 3, a directional axis 361 of a radiation pattern 360 of the point light source 313 that is included in a surface light source 312, a second directional axis 363 of a second radiation pattern 362 of the point light source 314 that is included in the surface light source 312, and the optical axis of the irradiation optical system 311 intersect with each other at the same position. Such arrangement enables the terahertz waves that are generated from the point light sources to be contained in an optically effective region of the irradiation optical system 311. Consequently, the vignetting that is caused by the irradiation optical system 311 is reduced, and the outputs of the terahertz waves that reach the object 140 can be inhibited from decreasing.

According to the present embodiment, the position at which the directional axis 361 intersects with the optical axis of the irradiation optical system 311 is the same as the position at which the directional axis 363 intersects with the optical axis of the irradiation optical system 311. However, the present embodiment is not limited to this structure. That is, the directional axes 361 and 363 may intersect with the optical axis of the irradiation optical system 311 at different positions.

The terahertz waves from the point light sources are preferably radiated to the object 140 at the same time. In the case where the outputs of the first point light source 113 and the second point light source 114 are modulated, the point light sources preferably change the outputs to the object 140 synchronously.

Figure 10A:
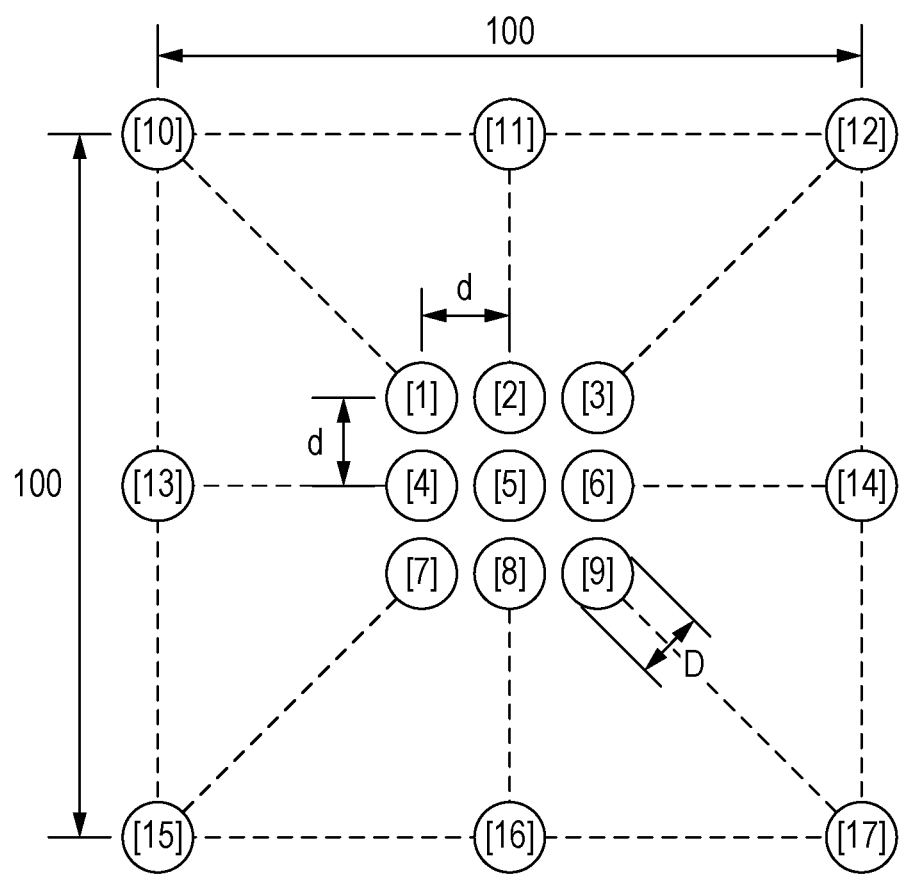
FIG. 10A schematically illustrates an example of calculation of beam distribution of the image capture device according to the first embodiment.
Figure 10B:
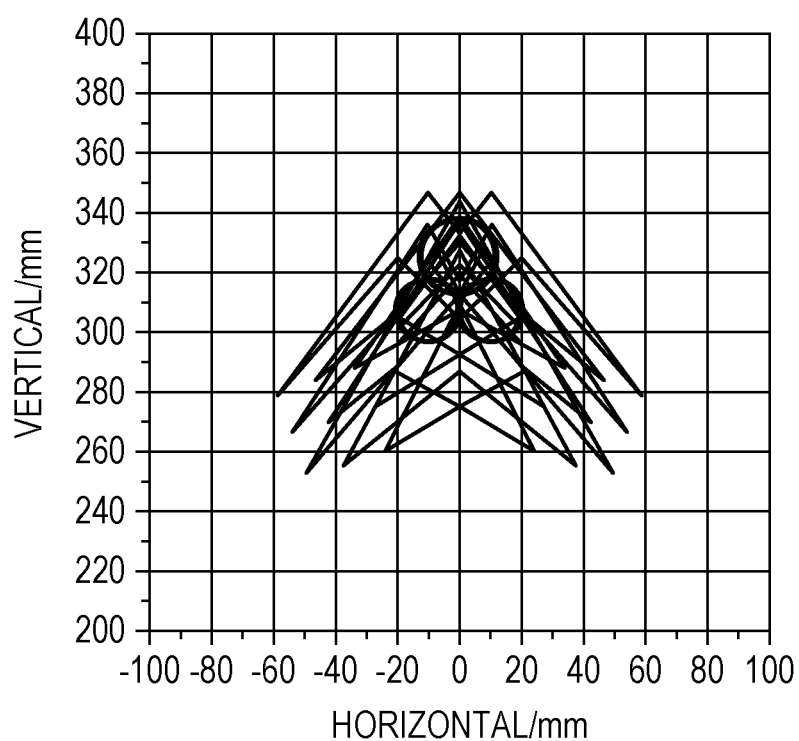
FIG. 10B schematically illustrates an example of calculation of the beam distribution of the image capture device according to the first embodiment.
Figure 10C:
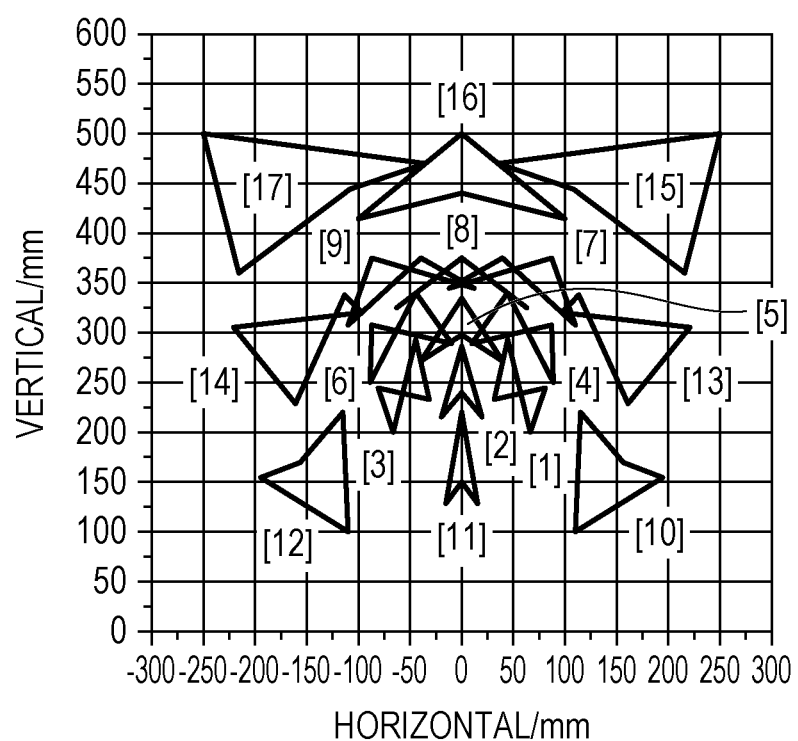
FIG. 10C schematically illustrates an example of calculation of the beam distribution of the image capture device according to the first embodiment.

FIG. 10B and FIG. 10C illustrate examples of geometrical optics calculation of the beam patterns of the terahertz waves that are imaged on the imaging plane 215 of the image capture device 1002 in FIG. 2 from the surface light source 212. Specifically, rays are tracked from the point light sources that are included in the surface light source 212 to the imaging plane 215.

FIG. 10A illustrates the arrangement of the point light sources that are included in the surface light source 212 that is used for the calculation. The surface light source 212 is used for the calculation on assumption that the surface light source 212 includes point light sources [1] to [9] that are arranged at a central portion of the surface light source 212 and that are arranged d spaced apart from each other, and point light sources [10] to [17] that are arranged on an outer circumferential portion of the surface light source 212. The point light sources [1] to [9] at the central portion are used to see overlap between the beam distributions of the terahertz waves. The point light sources [10] to [17] on the outer circumferential portion are used to see the maximum expansion of the beam distributions due to the aberration.

For simplicity of the calculation, here, the surface light source 212 includes the nine point light sources [1] to [9] that are arranged at the central portion and the eight point light sources [10] to [17] that are arranged on the outer circumferential portion. However, the number and position of the point light sources are not limited thereto. For example, in the case where the point light sources are distance d spaced apart from each other and arranged in a matrix shape, the number of the point light sources of the surface light source 212 may be (L/d+1)×(L/d+1) where L is the length of an outer circumferential side of the surface light source 212.

The conditions for the calculation will be described. In FIG. 10A, the length L of the side of the surface light source 212 is 100 mm. In the case where the target frequency is 0.5 THz, the wavelength λ of the terahertz waves is 0.6 mm. A half-wavelength antenna is used as the antenna of each point light source. The diameter D of the antenna is 0.3 mm. In this case, the far field of the antenna is 0.3 mm (λ/2) or more. The far field that is considered as infinity is 4.8 mm (8λ) or more.

A typical parabolic antenna for satellite broadcasting is used as the irradiation optical system 211. The length of an aperture of the parabolic antenna in the longitudinal direction is 520 mm and the length thereof in the transverse direction is 460 mm. The depth from the aperture to the bottom is 50 mm. The on-axis focal length of the parabolic antenna is 234 mm, the off-axis angle thereof is 55.6 degrees, and the off-axis focal length thereof is 299 mm.

The off-axis focus of the parabolic antenna that serves as the irradiation optical system 211 is located on the incidence axis 250 of the terahertz waves that reach the irradiation optical system 211 from the surface light source 212. The inclination of the aperture of the irradiation optical system 211 is 62.2 degrees with respect to the incidence axis 250. The incidence axis 250 corresponds to a geometrically optical axis. The object plane 216 is perpendicular to the incidence axis 250. The object plane 216 passes through a point on the incidence axis 250. Specifically, the object plane 216 is located at a position about 85 mm from the off-axis focus in the direction away from the irradiation optical system 211. The surface light source 212 is disposed near the object plane 216 such that the object plane 216 and the resting plane 217 intersect with each other. The resting plane 217 may match the object plane 216.

In the case where such a first irradiation unit 210 is used, the first irradiation waves 253 are imaged on a location about 1340 mm away from the irradiation optical system 211, and the terahertz waves are radiated to the object 140. When the length L of the outer circumferential side of the surface light source 212 is 100 mm as described above, the first irradiation waves 253 that are radiated to the object 140 have a dimension of about 350 mm×350 mm. In the calculation, the effective diameter of the aperture of the parabolic antenna is 80%. The second irradiation unit 220 has the same structure as the first irradiation unit 210.

FIG. 10B illustrates calculation of the beam distributions, on the imaging plane 215, of the terahertz waves from the point light sources [1] to [9] at the central portion of the surface light source 212 when the distance d between the point light sources is 4.8 mm (8λ), which is considered as infinity of each antenna. The horizontal axis (Horizontal/mm) corresponds to the X-direction in FIG. 2, and the vertical axis (Vertical/mm) corresponds to the Y-direction in FIG. 2.

As illustrated in FIG. 10B, the beam distributions of the terahertz waves extend so as to protrude upward because of an effect of the aberration of the parabolic antenna. It can be seen that the beams of the terahertz waves from the point light sources [1] to [4] and [6] to [9] around the point light source [5] overlap the beams of the terahertz waves from the point light source [5] that is disposed at the center. Consequently, the reflected waves 155 can be used as pseudo scattering waves. The reflected waves 155, which are the pseudo scattering waves that are reflected at the overlap portion, can be detected in a manner in which the observation region 160 of each pixel of the sensor 102 of the detection unit 100 is caused to overlap the overlap portion.

It is here assumed that a lens that has an outer diameter of 120 mm and a curvature of about 100 mm is used as the imaging optical system 101 and the distance between the sensor 102 and the imaging optical system 101 is 224 mm. In this case, the distance between the imaging optical system 101 and the object 140 is about 1200 mm and can be substantially equal to the distance between the first irradiation unit 210 and the object 140. When the pixel size of the sensor 102 is 0.5 mm, which is substantially equal to the wavelength of the surface light source 212, the size of the observation region 160 is about 2.6 mm. In FIG. 10B, the size of the overlap region (region illustrated in a circle in FIG. 10B) of the beam distributions is larger than the size of the observation region 160. For this reason, it can be understood that the overlap region can contain the observation region 160. The shape of the imaging optical system 101 may include an aspherical surface.

FIG. 10C illustrates the result of the calculation of the beam distributions of the terahertz waves from the point light sources [1] to [17] when the distance d between the point light sources is 19.2 mm (32λ). The number in the figure is the number of each point light source that is illustrated in FIG. 10A and that is used for the calculation. As illustrated in FIG. 10C, the beams of the terahertz waves from the point light source [5] that is disposed at the center overlap the beams of the terahertz waves from the point light sources [1] to [4] and [6] to [9] around the point light source [5] at two positions. Specifically, the beams of the terahertz waves of the point light source [5] overlap the beams from the terahertz waves from the point light sources [4] and [6].

The beam distributions of the terahertz waves from the point light sources [10] to [17] on the outer circumferential portion of the surface light source 212 are larger than the beam distributions of the point light sources [1] to [9] at the central portion due to the effect of the aberration of the irradiation optical system 211. For this reason, the number of the point light sources the beam distributions of which overlap the observation region 160 can be increased.

An overlap ratio of the terahertz waves from the adjacent point light sources will now be described. The "overlap ratio" in the specification is a ratio B/A of the number B of regions that overlap the beam at the central portion to the number A of the beams of the terahertz waves from the point light sources that are adjacent to the point light source that is disposed at the center, and is a ratio of the adjacent beam distributions that overlap. In the case in FIG. 10B, the distance d between the point light sources is 4.8 mm (8λ), and the overlap ratio is 1. In the case in FIG. 10C, the distance d between the point light sources is 19.2 mm (32λ), and the overlap ratio is 0.25.

Figure 11:
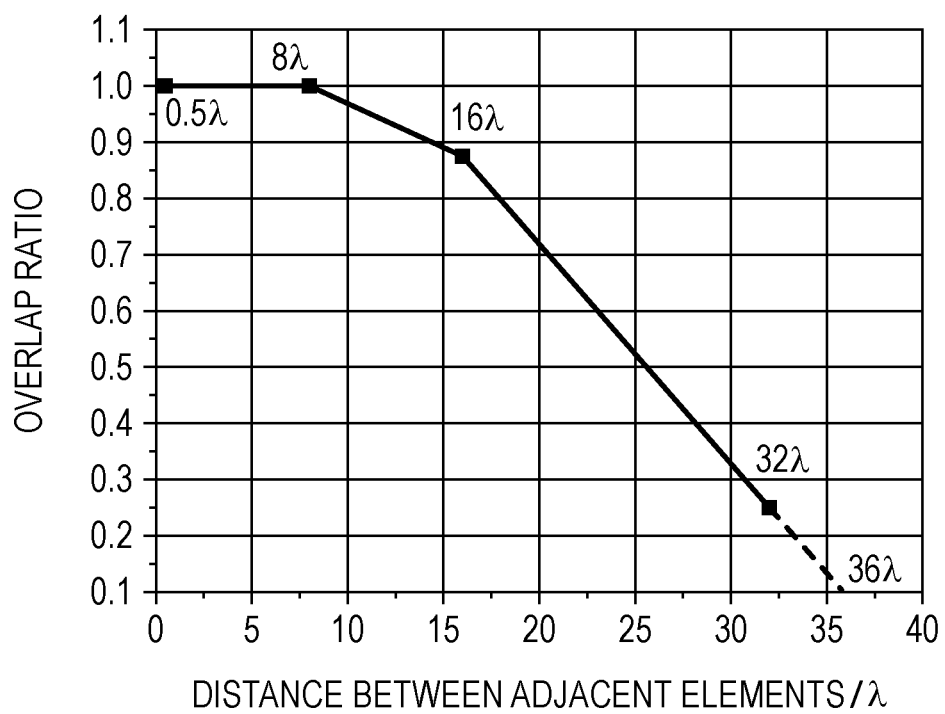
FIG. 11 illustrates a relationship between an overlap ratio of the beam distribution and a distance between the point light sources of the image capture device according to the first embodiment.

In FIG. 11, the overlap ratio between the adjacent beams is plotted for the distance d of the adjacent point light sources at the central portion of the surface light source 212. As illustrated in FIG. 11, all of the beams of the terahertz waves from the adjacent point light sources overlap within the far field 8λ that is considered as infinity, and the overlap ratio of the beams decreases outside 8λ. The beams scarcely overlap outside 32λ. The beam distributions are isolated from each other at 36λ.

It can be understood from above that the distance between the first point light source 113 and the second point light source 114 that is preferable to form the pseudo scattering waves at the terahertz wave band can be defined by the value of the far field that is defined by the wavelength λ. Specifically, as illustrated in FIG. 10C, the distance d between the first point light source 113 and the second point light source 114 is preferably no less than 0.5λ and no more than 36λ in order to form the pseudo scattering waves in the wavelength range of the terahertz waves. The distance d between the first point light source 113 and the second point light source 114 is more preferably no less than 0.5λ and no more than 8λ. The structure of the irradiation units 210 and 220 and the detection unit 100 is not limited to the above structure and is appropriately designed in accordance with components that are used in the image capture device and the shape of the object 140 to be observed.

With this structure, the pixels of the sensor of the camera can receive the specular reflection light in different directions by radiating the terahertz waves to the object in different directions. This enables the terahertz waves that are reflected from the observation region to be considered as the pseudo scattering waves. For this reason, the percentage of the pixels that cannot detect the terahertz waves can be decreased. Consequently, the resolution of the image that is captured by using the terahertz waves is improved, and the shape of the object can be readily presumed.

Second Embodiment

Figure 4:
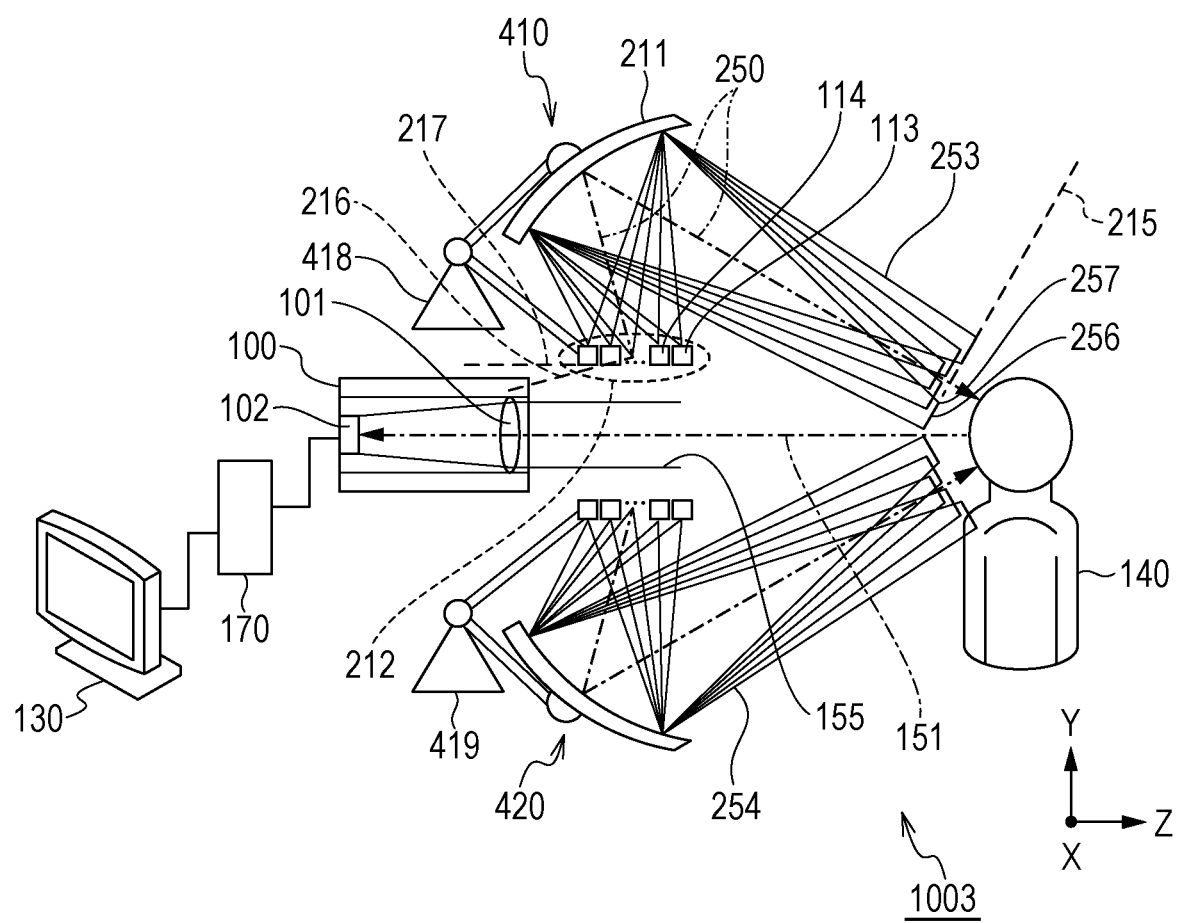
FIG. 4 schematically illustrates the structure of an image capture device according to a second embodiment.

An image capture device 1003 according to the present embodiment will be described with reference to FIG. 4. FIG. 4 schematically illustrates the structure of the image capture device 1003. The image capture device 1003 differs from the image capture device 1002 according to the first embodiment in that irradiation units 410 and 420 are arranged in a different manner. Common components to those according to the above embodiment are designated by like reference characters in FIG. 4, and a detailed description thereof is omitted.

In the image capture devices 1001 and 1002 according to the first embodiment, the irradiation units 110, 120, 210, and 220 and the detection unit 100 are combined together by the first support unit 118 and the second support unit 119. However, in the image capture device 1003 according to the present embodiment, the first irradiation unit 410 is held by a first support unit 418 and disposed separately from the detection unit 100. The second irradiation unit 420 is held by a second support unit 419 and disposed separately from the detection unit 100. The first support unit 418 and the second support unit 419 may hold the postures of the first irradiation unit 410 and the second irradiation unit 420 and may have a posture adjustment mechanism for adjusting the posture.

The image capture device according to the present embodiment, which uses the terahertz waves, can inhibit the number of the pixels that can detect the terahertz waves from decreasing.

With the structure of the image capture device 1003 according to the present embodiment, the degree of freedom of the arrangement of the first irradiation unit 410 and the second irradiation unit 420 is improved, and the image capture device can be used for a wider range of applications.

Third Embodiment

Figure 5:
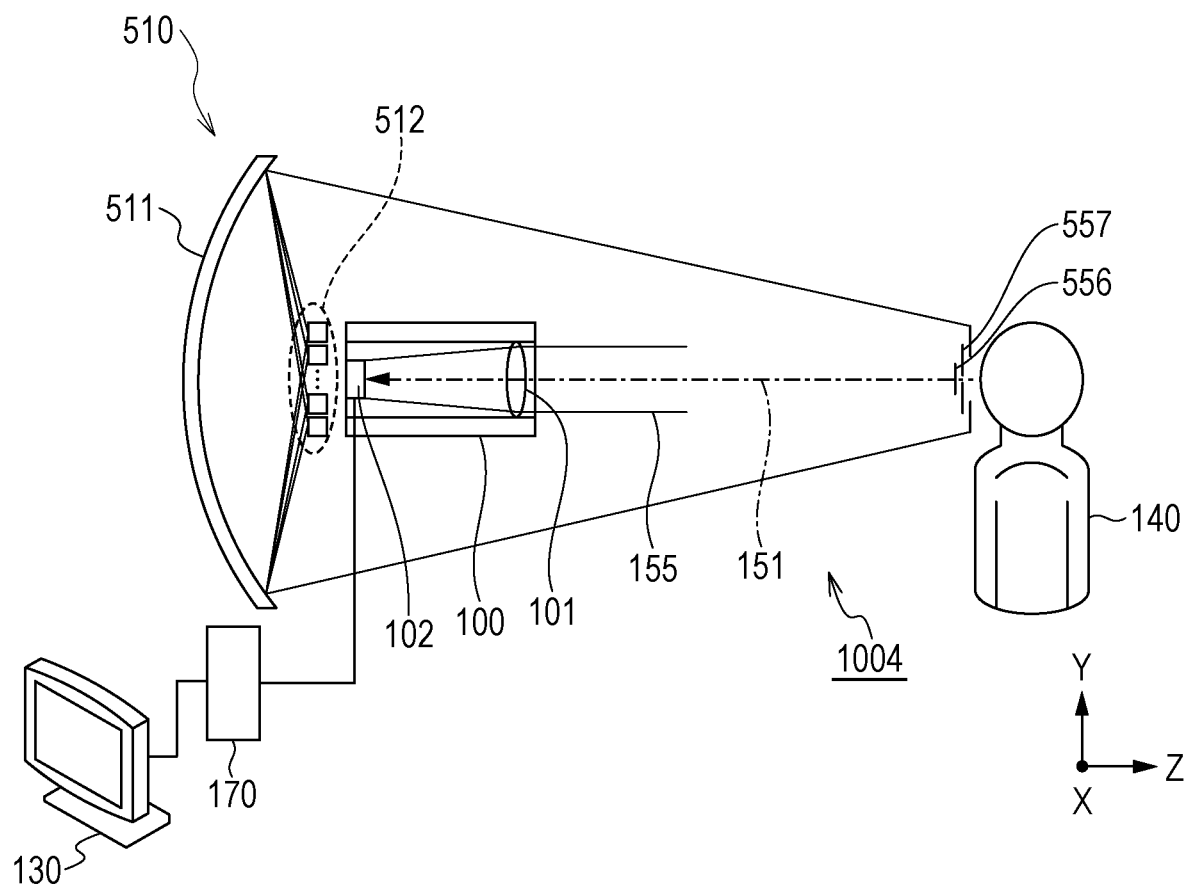
FIG. 5 schematically illustrates the structure of an image capture device according to a third embodiment.

The structure of an image capture device 1004 according to the present embodiment will be described with reference to FIG. 5. FIG. 5 schematically illustrates the structure of the image capture device 1004. The positional relationship between an irradiation unit 510 and the detection unit 100 of the image capture device 1004 differs from that according to the above embodiment. Common components to those according to the above embodiments are designated by like reference characters in FIG. 5, and a detailed description thereof is omitted.

Specifically, the irradiation unit 510 of the image capture device 1004 is disposed behind the detection unit 100. In other words, the imaging optical system 101 and an irradiation optical system 511 face each other with a surface light source 512 interposed therebetween, and the irradiation unit 510 is disposed such that the axis substantially coincides with the optical axis of the detection unit 100.

In this case, the irradiation optical system 511 of the irradiation unit 510 is preferably reflective, and the size of an optically effective region of the irradiation optical system 511 is preferably sufficiently larger than the size of a section of the detection unit 100. The irradiation unit 510 and the detection unit 100 may be integrally formed or may separate from each other. With this structure, the size of the image capture device 1004 can be decreased.

Also, according to the present embodiment, a first terahertz wave 556 and a second terahertz wave 557 from the point light sources of the irradiation unit 510 overlap on the imaging plane of the irradiation optical system 511. This enables the image capture device according to the present embodiment, which uses the terahertz waves, to inhibit the number of the pixels that can detect the terahertz waves from decreasing.

Fourth Embodiment

An image capture device 1005 according to the present embodiment will be described with reference to FIG. 6. FIG. 6 schematically illustrates the structure of the image capture device 1005. The image capture device 1005 is an equivalent to one of the image capture devices according to the above embodiments that further includes a structure for scanning the terahertz waves. An example described here is the image capture device 1002 according to the first embodiment that further includes the structure for scanning the terahertz waves. Common components to those according to the above embodiments are designated by like reference numbers in FIG. 6, and a detailed description is omitted.

The image capture device 1002 according to the first embodiment includes no mechanisms for scanning the terahertz waves, and the direction in which the terahertz waves are radiated to the object 140 is almost fixed, or a posture control unit, not illustrated, controls the postures of the irradiation units 210 and 220 to change the direction of the irradiation waves. The present embodiment, however, further includes a scanning unit 690 that scans the irradiation waves by simultaneously changing the postures of the first irradiation unit 210, the second irradiation unit 220, and the detection unit 100. Consequently, the incident angles and radiation ranges of the terahertz waves to the object 140 can be changed. Since the incident angles of the terahertz waves that are incident on the observation region 160 of each pixel of the sensor 102 can be changed, the reflection angles of the terahertz waves from the observation region 160 are also changed.

Figure 6A:
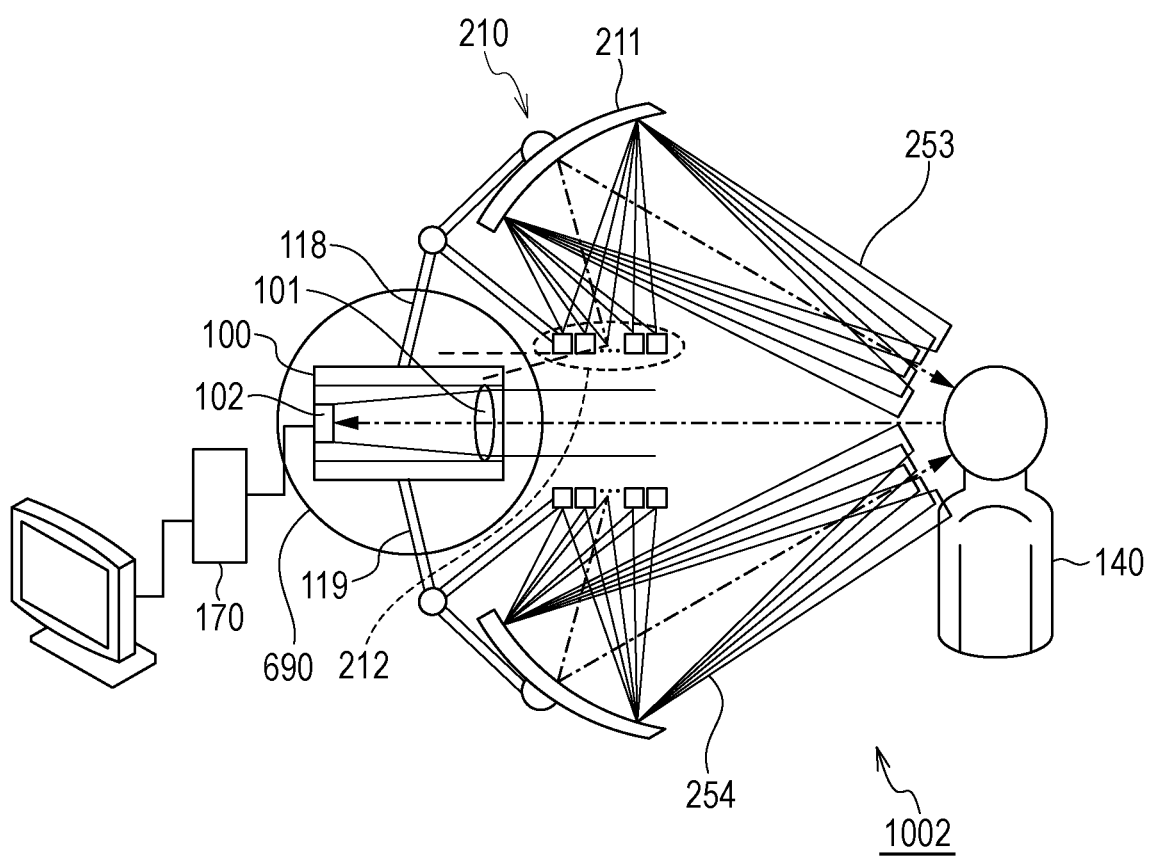
FIG. 6A schematically illustrates the structure of a scanning unit of an image capture device according to a fourth embodiment.
Figure 6B:
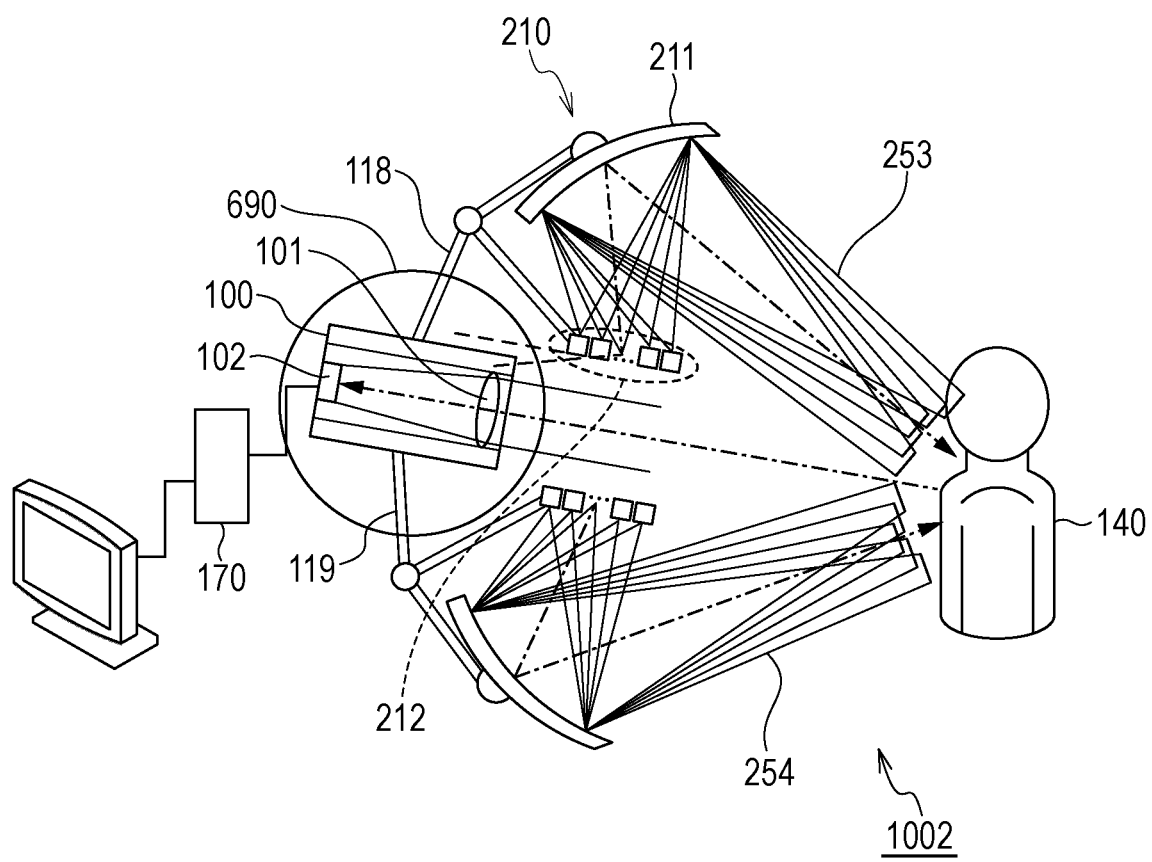
FIG. 6B schematically illustrates the structure of the scanning unit of the image capture device according to the fourth embodiment.

Examples of the scanning unit 690 can include an angle adjustment stage that adjusts an angle of elevation and an angle of direction (rotation angle) and a linear motion stage that adjusts the position of the image capture device 1002. According to the present embodiment, a rotation stage that adjusts the angle of elevation is used as the scanning unit 690. As illustrated in FIG. 6A and FIG. 6B, the positions and angles of radiation of the first irradiation waves 253 and the second irradiation waves 254 to the object 140 can be changed by simultaneously adjusting the postures of the first irradiation unit 210, the second irradiation unit 220, and the detection unit 100 by the scanning unit 690.

Here, the state in FIG. 6A is referred to as a first state, and the state in FIG. 6B is referred to as a second state. The image capture device 1005 obtains the detection result of the detection unit 100 in the first state and the detection result of the detection unit 100 in the second state and captures images from the respective detection results. The images are combined with each other. Consequently, reflection angle components of the terahertz waves that travel from the point light sources and that are reflected from the observation region 160 can be increased, and a state closer to scattering light can be obtained.

Figure 7:
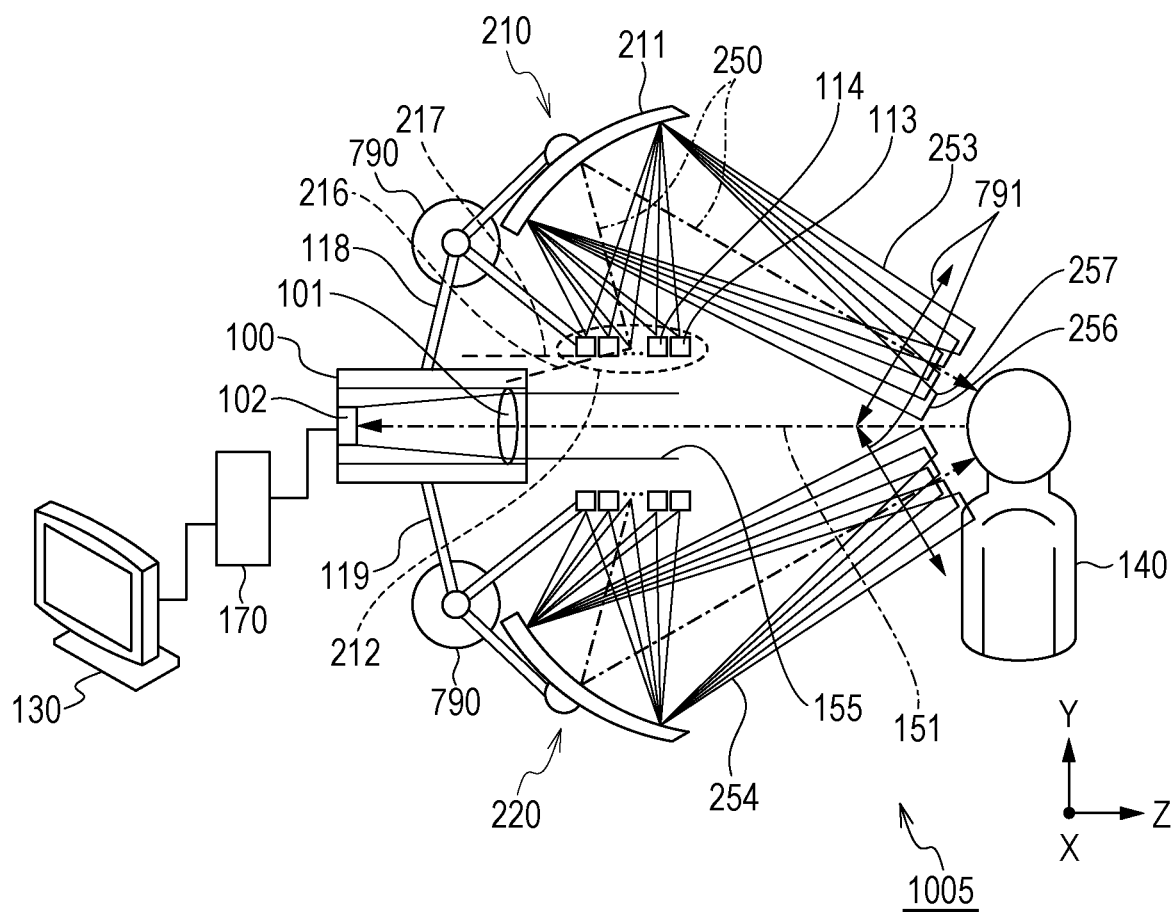
FIG. 7 schematically illustrates an example of another structure of the scanning unit of the image capture device according to the fourth embodiment.

The structure of the scanning unit 690 is not limited thereto. For example, as illustrated in FIG. 7, posture change units 790 of the first support unit 118 and the second support unit 119 can be used as the scanning unit 690. The posture change units 790 are mechanisms for changing the postures of the first irradiation unit 210 and the second irradiation unit 220. The posture change units 790 changes and adjusts the angles of elevation of the first irradiation unit 210 and the second irradiation unit 220 to scan the first irradiation waves 253 and the second irradiation waves 254 in scanning directions 791. The posture change unit 790 can be installed in the first support unit 418 or the second support unit 419 of the image capture device 1003 according to the second embodiment, or the posture change units 790 can be installed in both of the first support unit 418 and the second support unit 419.

Figure 12:
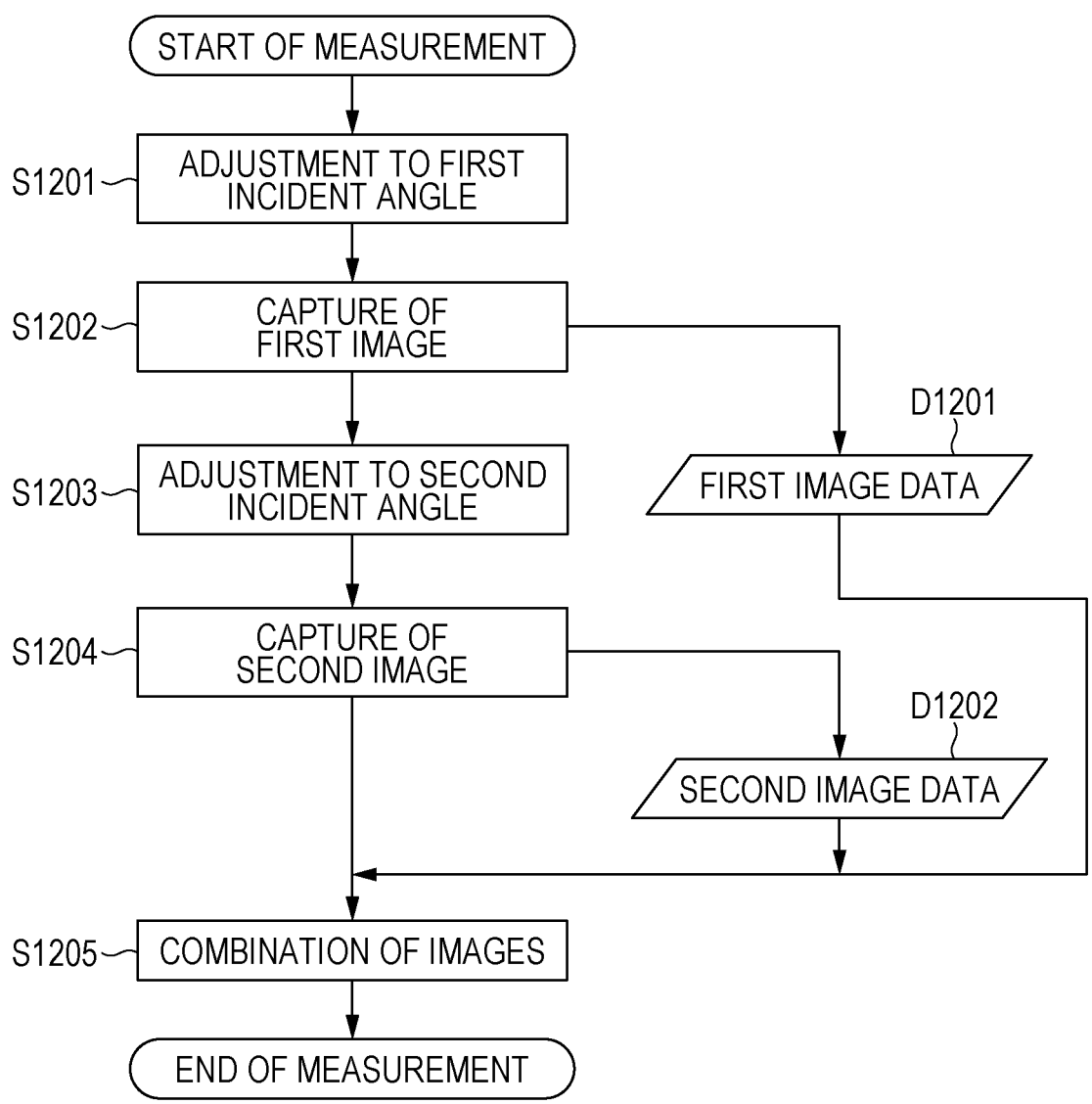
FIG. 12 is a flowchart illustrating a method of capturing an image according to the fourth embodiment.

A method of capturing an image by using the image capture device 1005 according to the present embodiment will be described with reference to FIG. 12. The incident angles of the irradiation waves on the object 140 are adjusted by the scanning unit 690 and include at least a first incident angle and a second incident angle. The number of the incident angles can be set by a measurer as needed or may be determined in advance in accordance with a measurement mode. In the following description, attention is paid to the first irradiation waves 253. However, the same processes may be performed for the other irradiation waves.

When measurement is started, the scanning unit 690 adjusts the postures such that the incident angles of the irradiation waves 253 on the object 140 are equal to the first incident angle (S1201). In this state, the irradiation waves 253 are radiated to the object 140, and the detection result that is obtained by detecting the reflected waves 155 from the object 140 by the detection unit 100 is used to capture a first image (S1202). First image data D1201 is stored in a storage unit of the processing unit. Subsequently, the scanning unit 690 adjusts the postures such that the incident angles of the irradiation waves 253 on the object 140 are equal to the second incident angle (S1203).

In this state, the irradiation waves 253 are radiated to the object 140, and the detection result that is obtained by detecting the reflected waves 155 from the object 140 by the detection unit 100 is used to capture a second image (S1204). Second image data D1202 is stored in a storage unit of the processing unit. This process is repeated the same number of times as the number of the incident angles that are set to capture the images.

Subsequently, the processing unit reads the first image data D1201 and the second image data D1202 that are stored in the storage unit, not illustrated, and combines the images (S1205). In this manner, the reflection angle components of the terahertz waves that are reflected from the observation region 160 can be increased, and a state closer to scattering light can be obtained. Consequently, the percentage of the pixels that cannot detect the terahertz waves can be decreased. Consequently, an image that has higher resolution than that in the conventional case can be captured, and the shape of the object can be readily presumed from the captured image. The monitor unit 130 can display the combined image.

The method of capturing an image described according to the present embodiment is an example, and the order of each step can be changed. Multiple steps can be performed at the same time. The step of capturing the image such as the step S1202 may be omitted, and information about the image that is captured at the step S1204 may be obtained from the detection results of the detection unit 100 that are obtained with different postures.

Figure 8:
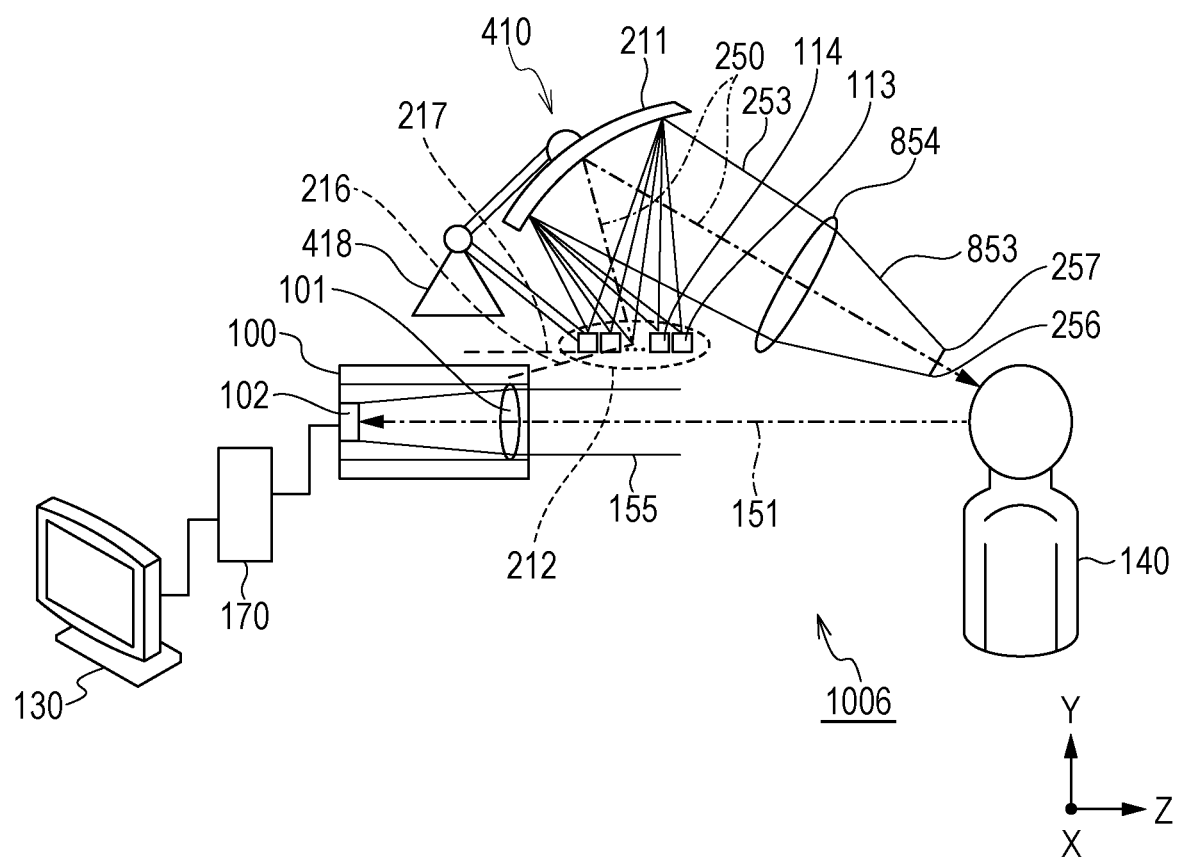
FIG. 8 schematically illustrates the structure of a shape adjustment unit of the image capture device according to the fourth embodiment.

In the case of the image capture devices described above, the first irradiation waves (153, 253) that include the first terahertz wave (156, 256) and the second terahertz wave (157, 257) are imaged on the object 140 in a circular plane as illustrated in FIG. 1B. However, the first irradiation waves 153 and 253 are not limited thereto and can be converged linearly. For example, as illustrated in FIG. 8, a shape adjustment unit 854 can be disposed on the optical axis (incidence axis 250) of the irradiation optical system 211 between the irradiation optical system 211 and the object 140, and the first irradiation waves 253 can be irradiation waves 853 that have linear beam distribution.

The shape adjustment unit 854 can be an optical element in which the curvature of the axis of one of the irradiation optical system 211 and the imaging optical system 101 differs from the curvature of the axis of the other optical system that is perpendicular to the axis. Examples thereof can include a cylindrical lens or a cylindrical mirror. In FIG. 8, a cylindrical lens through which the terahertz waves pass is used as the shape adjustment unit 854. The shape of the irradiation waves that is adjusted by the shape adjustment unit 854 is not limited to a linear shape and may be a circular shape or a quadrilateral shape.

The beam shape of the first irradiation waves 253, which are the terahertz waves, is thus concentrated to irradiate the object 140 therewith. This enables the outputs of the terahertz waves that are radiated to the observation region 160 can be increased. Consequently, the SN ratio of the terahertz waves that are obtained by an image capture device 1006 is improved, and the gradation of the image of the object that is captured by using the terahertz waves is improved.

Figure 9:
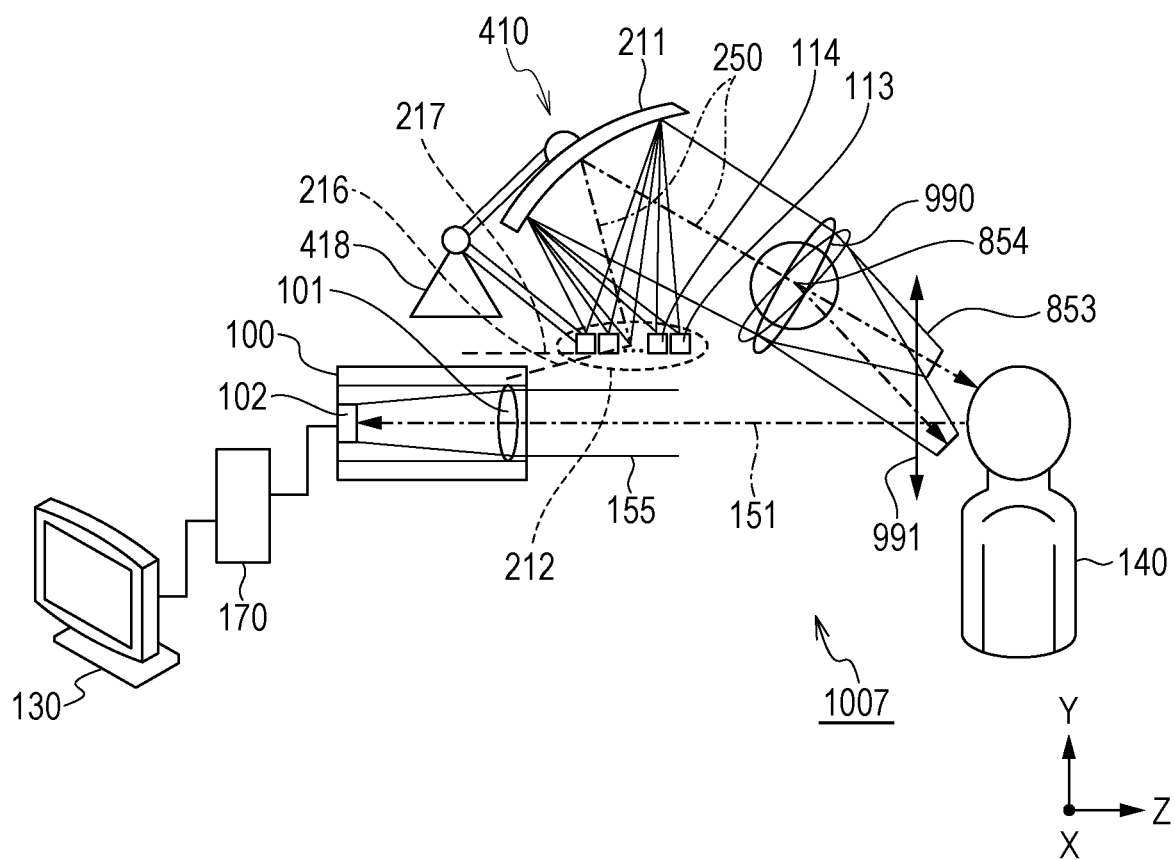
FIG. 9 schematically illustrates an example of another structure of the scanning unit of the image capture device according to the fourth embodiment.

In the case where the image capture device includes the above shape adjustment unit 854, as illustrated in FIG. 9, a scanning unit 990 that controls the posture of the shape adjustment unit 854 may be included. For example, in FIG. 9, the scanning unit 990 can scan the irradiation waves 853 in a scanning direction 991 by adjusting the angle of elevation of the shape adjustment unit 854.

With this structure, the reflection angle components of the terahertz waves that are radiated from the point light sources and that are reflected from the observation region 160 of the object 140 can be increased, and a state closer to scattering light can be obtained. This enables the image capture device according to the present embodiment, which uses the terahertz waves, to inhibit the number of the pixels that can detect the terahertz waves from decreasing. Consequently, the percentage of the pixels that cannot detect the terahertz waves can be decreased, and the shape of the object can be readily presumed from the obtained terahertz wave image.

Preferred embodiments of the present invention are described above. The present invention, however, is not limited to the embodiments, and various modifications and alterations can be made within the range of the spirit thereof. The structures of the image capture devices according to the above embodiments can be combined for use. Accordingly, a new image capture device may be obtained by appropriately combining various techniques according to the above embodiments. The image capture device that is obtained by the combination is also included in the scope of the present invention.

The present invention is not limited to the above embodiments. Various modifications and alterations can be made without departing from the spirit and scope of the present invention. Accordingly, the following claims are attached to make the scope of the present invention public.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An image capture device that captures an image by using a terahertz wave, the image capture device comprising:
    a generating unit that includes a plurality of generation elements each of which generates the terahertz wave and rests on a resting plane;
    an irradiation optical system that irradiates an object with the terahertz wave from the generating unit;
    an imaging optical system that images the terahertz wave that is reflected from the object; and
    a sensor that includes pixels and that detects the terahertz wave from the imaging optical system,
    wherein the plurality of generation elements include at least a first generation element and a second generation element that have different angles of radiation to the object, and
    wherein there is an overlap region in which a region of radiation of a first terahertz wave from the first generation element to the object overlaps a region of radiation of a second terahertz wave from the second generation element to the object.

2. The image capture device according to claim 1, wherein the overlap region overlaps an observation region that corresponds to at least one of the pixels on an imaging plane of the irradiation optical system.

3. The image capture device according to claim 1, wherein at least a part of the generating unit rests on an object plane of the irradiation optical system.

4. The image capture device according to claim 1,
wherein the resting plane and the object plane intersect with each other.

5. The image capture device according to claim 4,
wherein the resting plane includes a curved surface.

6. The image capture device according to claim 1,
wherein the first generation element rests such that a first directional axis of a radiation pattern of the first terahertz wave intersects with an optical axis of the irradiation optical system, and
wherein the second generation element rests such that a second directional axis of a radiation pattern of the second terahertz wave intersects with the optical axis of the irradiation optical system.

7. The image capture device according to claim 1,
wherein the irradiation optical system and the imaging optical system are coaxial with each other with the generating unit interposed therebetween.

8. The image capture device according to claim 1,
wherein a distance between two adjacent generation elements is no less than $0.5\lambda$ and no more than $36\lambda$, where $\lambda$ is a longest wavelength of wavelengths of terahertz waves from the two adjacent generation elements of the plurality of generation elements.

9. The image capture device according to claim 8,
wherein the distance between the two adjacent generation elements is no less than $0.5\lambda$ and no more than $8\lambda$.

10. The image capture device according to claim 1,
wherein the first generation element and the second generation element are adjacent to each other.

11. The image capture device according to claim 1, further comprising:
a scanning unit that changes an incident angle of the terahertz wave that is incident from the generating unit on the object from a first incident angle into a second incident angle; and
a processing unit that captures an image of the object by using a detection result of a detection unit at the first incident angle and a detection result of the detection unit at the second incident angle.

12. The image capture device according to claim 1,
wherein the irradiation optical system includes a transmissive optical element.

13. The image capture device according to claim 1,
wherein the irradiation optical system includes a reflective optical element.

14. The image capture device according to claim 1,
wherein the terahertz wave from the generating unit includes a terahertz wave at no less than 0.3 THz and no more than 30 THz.

15. The image capture device according to claim 1,
wherein the terahertz wave from the generating unit includes a terahertz wave at no less than 0.3 THz and no more than 1 THz.

16. An irradiation device comprising:
a generating unit that includes a plurality of generation elements each of which generates a terahertz wave and rests on a resting plane; and
an irradiation optical system that irradiates an object with the terahertz wave from the generating unit,
wherein the plurality of generation elements include at least a first generation element and a second generation element that have different angles of radiation to the object, and
wherein there is an overlap region in which a region of radiation of a first terahertz wave from the first generation element to the object overlaps a region of radiation of a second terahertz wave from the second generation element to the object.

17. A method of capturing an image, the method comprising:
a first generation step of generating a first terahertz wave from a first generation element;
a second generation step of generating a second terahertz wave from a second generation element;
a convergence step of converging the first terahertz wave and the second terahertz wave on an object;
an imaging step of imaging the first terahertz wave and the second terahertz wave that are reflected from the object; and
a detection step of detecting the first terahertz wave and the second terahertz wave that are imaged at the imaging step,
wherein the first terahertz wave and the second terahertz wave overlap on the object.

* * * * *